(12) United States Patent
Goldfine et al.

(10) Patent No.: US 7,451,657 B2
(45) Date of Patent: Nov. 18, 2008

(54) MATERIAL CONDITION MONITORING WITH MULTIPLE SENSING MODES

(75) Inventors: Neil J. Goldfine, Newton, MA (US); Darrell E. Schlicker, Watertown, MA (US); Vladimir A. Zilberstein, Chestnut Hill, MA (US); Andrew P. Washabaugh, Chula Vista, CA (US); Volker Weiss, Syracuse, NY (US); Christopher A. Craven, Bedford, MA (US); Ian C. Shay, Waltham, MA (US); David C. Grundy, Reading, MA (US); Karen E. Walrath, Arlington, MA (US); Robert J. Lyons, Boston, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 103 days.

(21) Appl. No.: 11/036,780

(22) Filed: Jan. 14, 2005

(65) Prior Publication Data

US 2005/0171703 A1     Aug. 4, 2005

Related U.S. Application Data

(60) Provisional application No. 60/537,194, filed on Jan. 16, 2004.

(51) Int. Cl.
*G01B 5/30* (2006.01)
(52) U.S. Cl. .................................. 73/760; 324/228
(58) Field of Classification Search .................. 374/53, 374/54; 73/61.48, 61.49
See application file for complete search history.

(56) References Cited

U.S. PATENT DOCUMENTS 4,059,987 A * 11/1977 Dowling et al. ............ 73/61.43
4,281,533 A * 8/1981 Eesley et al. ............... 73/61.76
4,332,157 A   6/1982 Zemel et al.
4,341,113 A * 7/1982 Gutzwiller, Jr. .............. 73/105
4,453,405 A   6/1984 Zemel
4,551,425 A   11/1985 Zemel
4,656,869 A * 4/1987 Zacharias ..................... 73/597
4,814,690 A   3/1989 Melcher et al.

(Continued)

FOREIGN PATENT DOCUMENTS

FR     2 279 044    * 2/1976

*Primary Examiner*—Robert R Raevis
(74) *Attorney, Agent, or Firm*—Hamilton, Brook, Smith & Reynolds, P.C.

(57) ABSTRACT

Methods are described for assessing material condition. These methods include the use of multiple source fields for interrogating and loading of a multicomponent test material. Source fields include electric, magnetic, thermal, and acoustic fields. The loading field preferentially changes the material properties of a component of the test material, which allows the properties of the component materials to be separated. Methods are also described for monitoring changes in material state using separate drive and sense electrodes with some of the electrodes positioned on a hidden or even embedded material surface. Statistical characterization of the material condition is performed with sensor arrays that provide multiple responses for the material condition during loading. The responses can be combined into a statistical population that permits tracking with respect to loading history. Methods are also described for measuring the stress in the material by independently estimating effective electrical properties, such as magnetic permeability or electrical conductivity, using layered models or predetermined spatial distributions with depth that are then correlated with the stress.

21 Claims, 11 Drawing Sheets

U.S. PATENT DOCUMENTS

| | | | |
|---|---|---|---|
| 4,851,773 A * | 7/1989 | Rothstein | 324/220 |
| 5,453,689 A | 9/1995 | Golfine et al. | |
| 5,570,017 A * | 10/1996 | Blum | 324/232 |
| 5,793,206 A | 8/1998 | Goldfine et al. | |
| 6,063,264 A * | 5/2000 | Haritatos | 208/137 |
| 6,071,563 A * | 6/2000 | Kozlowski et al. | 427/374.7 |
| RE36,986 E | 12/2000 | Melcher | |
| 6,188,218 B1 | 2/2001 | Goldfine et al. | |
| 6,380,747 B1 | 4/2002 | Goldfine et al. | |
| 6,425,686 B1 * | 7/2002 | Zaldivar et al. | 374/16 |
| 6,486,673 B1 | 11/2002 | Goldfine et al. | |
| 6,514,631 B1 * | 2/2003 | Yamamoto et al. | 428/682 |
| 6,643,393 B1 * | 11/2003 | Van et al. | 382/145 |
| 6,657,429 B1 | 12/2003 | Goldfine et al. | |
| 6,734,668 B2 * | 5/2004 | Hils et al. | 324/232 |
| 6,781,387 B2 | 8/2004 | Goldfine et al. | |
| 6,784,662 B2 | 8/2004 | Schlicker et al. | |
| 2002/0075006 A1 | 6/2002 | Goldfine et al. | |
| 2002/0158626 A1 | 10/2002 | Shay et al. | |
| 2002/0163333 A1 | 11/2002 | Schlicker et al. | |
| 2004/0225474 A1 | 11/2004 | Goldfine et al. | |
| 2005/0083032 A1 | 4/2005 | Goldfine et al. | |

* cited by examiner

US 7,451,657 B2

MATERIAL CONDITION MONITORING WITH MULTIPLE SENSING MODES

RELATED APPLICATION

This application claims the benefit of U.S. Provisional Application No. 60/537,194, filed on Jan. 16, 2004.

The entire teachings of the above application are incorporated herein by reference.

BACKGROUND OF THE INVENTION

The technical field of this invention is that of nondestructive materials characterization, particularly quantitative, model-based characterization of surface, near-surface, and bulk material condition for flat and curved parts or components. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution.

Common methods for measuring the material properties use interrogating fields, such as electric, magnetic, thermal or acoustic fields. The type of field to be used depends upon on the nominal properties of the test material and the condition of interest, such as the depth and location of any features or defects. For relatively complicated heterogeneous materials, such as layered media, each layer typically has different properties so that multiple methods are used to characterize the entire material. However, when successively applying each method, there is no guarantee that each sensor is placed at the same distance to the surface or that the same areal material region is being tested with each method without careful registration of each sensor.

A relevant example is the condition of thermal barrier coatings (TBCs) used on critical engine components in the turbine section. Because of the severe environment in which they operate, turbine section components are subject to a variety of damage mechanisms during their service lives. Their typical operating temperature of up to 2000° F. causes migration of alloying elements and accelerates inward diffusion of oxygen. Oxidation of the bond coat can introduce substantial stress at the bond coat/ceramic interface and result in spallation of the ceramic top coat. The combination of this high operating temperature and the high mass flow rate experienced by the turbine blades results in thinning of the top coat, which can produce hot spots in the underlying blade or vane resulting in nonuniform degradation of the thermal barrier coating. Realistic assessment of the TBC condition, based on measured intrinsic properties can significantly reduce the life-cycle costs associated with these components.

Characterization of these coatings poses challenges because of the large number of variables associated with their layered construct. Variations in the properties and/or dimensions of the coatings or substrate have the potential to obscure other conditions. Characterization of TBCs and bond coats with conventional eddy current sensors is impractical due to the lack of sensor reproducibility, the difficulty in modeling the complex winding interactions with layered media, and the complex shape of turbine blade surfaces.

Conventional eddy-current sensing involves the excitation of a conducting winding, the primary, with an electric current source of prescribed frequency. This produces a time-varying magnetic field, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks.

Another example is the measuring of applied and residual stresses and detecting early stage fatigue damage. Highly stressed aircraft components, such as landing gear components, require the use of steels such as 4340 M and 300 M heat treated to very high strength levels. The integrity of these components is critical to the safe operation of aircraft and for maintaining readiness of military aircraft. However, unintentional loading of these components, such as a hard landing or during towing or taxiing, can impart residual stresses that compromise the integrity of the component.

Existing magnetic/electromagnetic, diffraction, ultrasonic and other methods for assessment of residual stresses in steel components or monitoring of applied stress over wide areas are not yet practical or cost-effective. Typically, discrete strain gages are mounted directly onto the material under test (MUT). However this requires intimate fixed contact between the strain gage and the MUT and individual connections to each of the strain gages, both of which limit the potential usefulness for monitoring stress over large areas. Furthermore, strain gages are limited in durability and do not always provide sufficient warning of gage failure or malfunction. Correlations between magnetic properties and stresses in ferromagnetic materials have been studied for over 100 years. Magnetostriction effect data suggests that, depending on the magnitude and sign of the magnetostriction coefficient, correlation between stress and magnetic permeability within certain ranges of the magnetic field should be present. However, attempts to use conventional inductive, i.e., eddy-current sensors for assessment of residual stresses as well as for a number of other applications have shown significant limitations, particularly for complex geometry components.

SUMMARY OF THE INVENTION

Aspects of the methods described herein involve nondestructive condition monitoring of materials. These conditions include stress, damage, damage precursor states and usage states. The material condition is typically assessed through correlations with independent estimates of material properties, such as electrical conductivity, dielectric permittivity, magnetic permeability, thermal conductivity, and effective layer thicknesses.

In an embodiment, a property is measured for a multicomponent test material by placing a sensor near the test material and interrogating the test material with a source field. The property is measured as a second source field, which may also be generated by the sensor, loads the test material to change a property of one of the component materials. Example source fields are magnetic fields, electric fields, and temperature or thermal fields. When the loading field is mechanical, the source field can be sonic or acoustic. Another example source is a laser. The source field for interrogating the test material may have a bias which alters the operating point for the property measurement, such as with a DC magnetic field on a magnetic material. The loading source field can be operated in a variety of manners, such as a transient or pulse, a steady-state (DC or AC) condition, or dynamically.

In another embodiment, the material condition or state is monitored using sensor or sensor arrays that have one or more conductors mounted on a hidden material surface. The sensor or sensor arrays have at least one conductor that can be driven to apply an interrogating field while at least one additional conductor, on an opposite side of the test material from the drive conductor creating the field, is used to sense the response of the test material to the field. In certain embodiments, the state is damage, usage, or corrosion. In an embodiment, both driven and sense conductors are placed on both sides of the test material, on both the near and hidden surfaces. The hidden material surface may be embedded between two material layers so that the only access to the sensor conductors is at the edges of the material. In another embodiment, the response is measured for multiple relative drive and sense positions, either with an embedded drive conductor and a sense conductor scanned over the surface or with an embedded sense conductor and the drive scanned over the surface.

In yet another embodiment, statistical characterization is performed by monitoring the material properties using multiple sensors or a sensor array and monitoring the load on a material. The multiple material responses are used to construct a population of responses that are tracked with the loading history. In certain embodiments, the loading history is assumed to be proportional to a time based measure, such as the number of flight hours or fatigue cycles. The loading can be mechanical so that the material properties change with fatigue. In an embodiment, the material properties are monitored during loading. Alternatively, the properties can be measured periodically between loads. In a further embodiment, the statistics of subpopulations can also be tracked, such as those relevant to a particular aircraft, number of flight hours, or a geographic location.

Another embodiment is the characterization of stress in materials through correlations with electrical property measurements. This is accomplished by placing a directional sensor near the material surface and measuring the response in at least two orientations and for at least two excitation frequencies. The directionality of the sensor then allows the orientation dependence of the material properties to be measured while the multiple frequency excitations allows the property variation with depth, preferably with a magnetic sensor, to be measured. The properties of the test material are obtained from a predetermined model for the spatial property variation with distance away from the sensor. In an embodiment, the model has two layers to represent two physical layers of a test material. A measurement of the magnetic permeability in one of the two layers can then provide a nondestructive assessment of the stress at the interface between the component layers. Alternatively, the stress can result from a cold work process, such as shot peening, and the spatial variation in properties can be represented by several layers, such as a machining affected zone, a residual stress zone, and a substrate.

In an embodiment, a magnetic field sensor or sensor array is used to estimate the properties of a near surface and hidden material layers. This type of layer geometry typically results from machining and cold working processes, such as shot peening, roller burnishing, low plasticity burnishing, laser shock peening. The result is a near surface machining affected zone over a deeper residual stress zone, both of which are on a substrate. The properties of the layers can be obtained from a model of each layer assuming a predetermined thickness, dependent upon the material type and expected processing intensity, and then sequentially estimating the properties of the near surface layer, then the hidden (e.g., residual stress) layer, and then the substrate. Preferably, these estimations are performed using a precomputed database of responses. In addition, the sensor may have an orientation dependence response and the response can be measured for multiple orientations that are varied incrementally or continuously.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

Multiple component material systems and multifunctional materials may be characterized using hybrid and "tribrid" sensing methods. These methods use a combination of methods for assessing the material condition or state by relying upon a loading condition which preferentially affects one of the component materials in the system along with an interrogating sensor field that monitors the condition of the material system. Example multiple component materials include TBCs and embedded fiber-matrix composites. Loading the material, in a static, transient, quasistatic, and/or dynamic fashion, varies the unknown composite material condition (e.g. fiber density, fiber or matrix temperature, stress) in a manner that varies one, a subset, or all of the measurable unknown and/or known properties in a prescribed or at least controlled manner. A variety of interrogating sensor and loading fields can be used. These fields can be scalar quantities, such as the temperature or electric potential, or vector quantities such as electric and magnetic fields.

Figure 1:
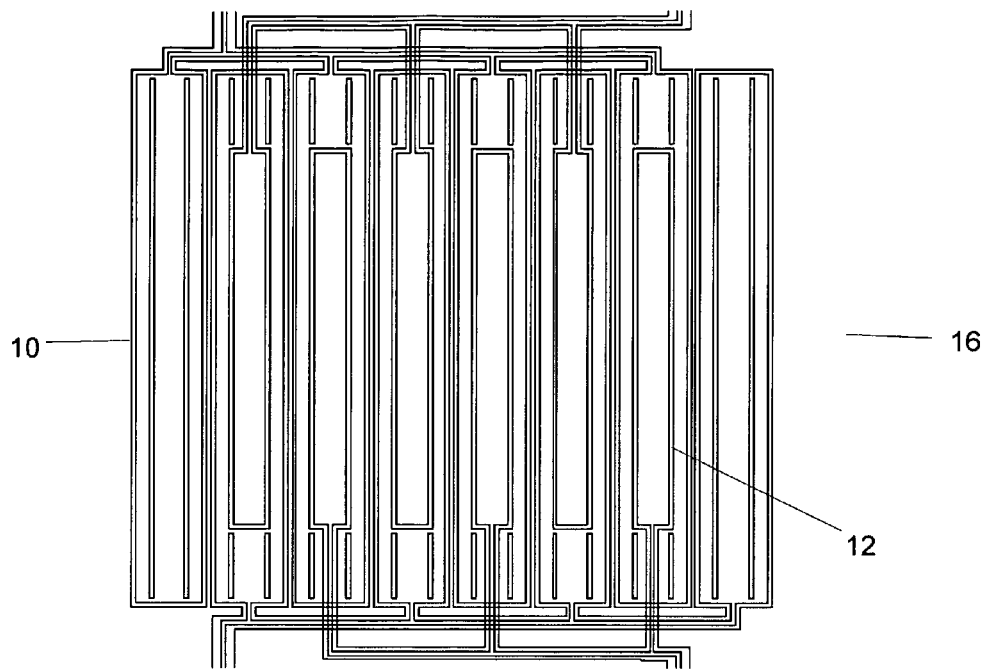
FIG. 1 shows a drawing of a spatially periodic field eddy-current sensor.

An example magnetic field sensor that operates in the magnetoquasistatic (MQS) regime is shown in FIG. 1. This meandering winding magnetometer (MWM®) is a "planar," conformable eddy-current sensor that was designed to support quantitative and autonomous data interpretation methods. The sensor 16 is described in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength $\lambda$. A current is applied to the primary winding to create a magnetic field and the response of the MUT to the magnetic field is determined through the voltage measured at the terminals of the secondary windings. This geometry creates a magnetic field distribution similar to that of a single meandering primary winding. A single element sensor has all of the sensing elements connected together. The net magnetic vector potential produced by the current in the primary can be accurately modeled as a Fourier series summation of spatial sinusoids, with the dominant mode having the spatial wavelength $\lambda$. For an MWM-Array, the responses from individual or combinations of the secondary windings can be used to provide a plurality of sense signals for a single primary winding construct as described in U.S. Pat. Nos. 5,793,206 and Re. 36,986, the entire teachings of which are incorporated herein by reference.

Figure 2:
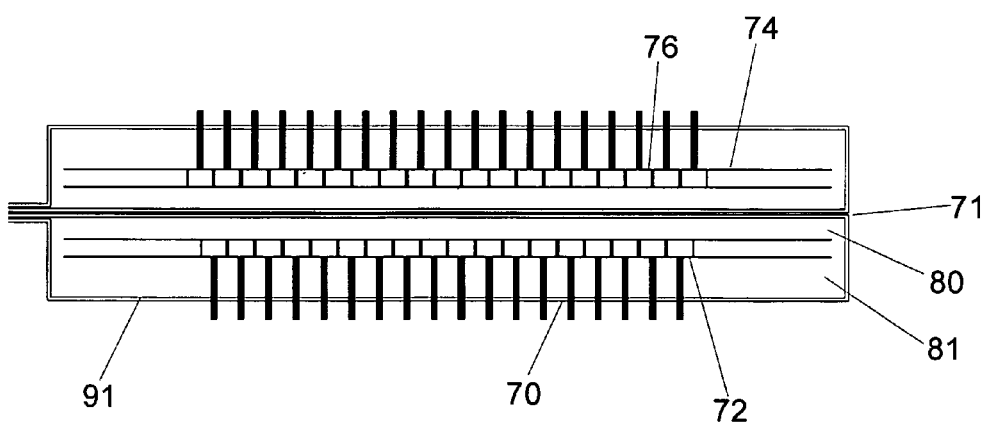
FIG. 2 shows a plan view of sensor array with a single primary winding and an array of sensing elements with connections to each individual element.

The MWM-Arrays typically have one or more drive windings, possibly a single rectangle, and multiple sensing elements for inspecting the test material. Some of the motivation for the use of multiple sensing elements is to increase the spatial resolution of the material being characterized without loss of coverage, to add additional information for use in the estimation of multiple unknown material properties, and to cover large inspection areas in a faster time. Example scanning sensor arrays are described in detail in U.S. patent application Ser. Nos. 10/102,620, filed Mar. 19, 2002, and 10/010,062, filed Mar. 13, 2001, the entire teachings of which are incorporated herein by reference. FIG. 2 shows a schematic view of a permanently mounted seven-element array. Connections are made to each of the individual secondary elements 61. Dummy elements 63 are placed on the outside meanders of the primary 65. As described in U.S. Pat. No. 6,188,218, the secondaries are set back from the primary winding connectors 67 and the gap between the leads to the secondary elements are minimized.

An efficient method for converting the response of the MWM sensor into material or geometric properties is to use grid measurement methods. These methods map two known values, such as the magnitude and phase or real and imaginary parts of the sensor impedance, into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for near real-time measurements of the absolute electrical properties of the material and geometric parameters of interest. The database of the sensor responses can be generated prior to the data acquisition on the part itself, so that only table lookup and interpolation operations, which are relatively fast, needs to be performed after measurement data is acquired. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 3:
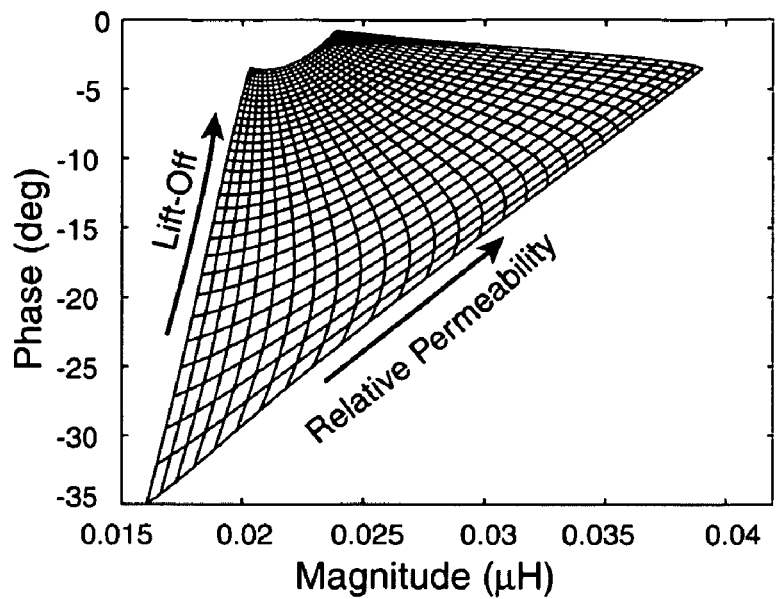
FIG. 3 shows a representative measurement grid relating the magnitude and phase of the sensor terminal impedance to the lift-off and magnetic permeability.
Figure 4:
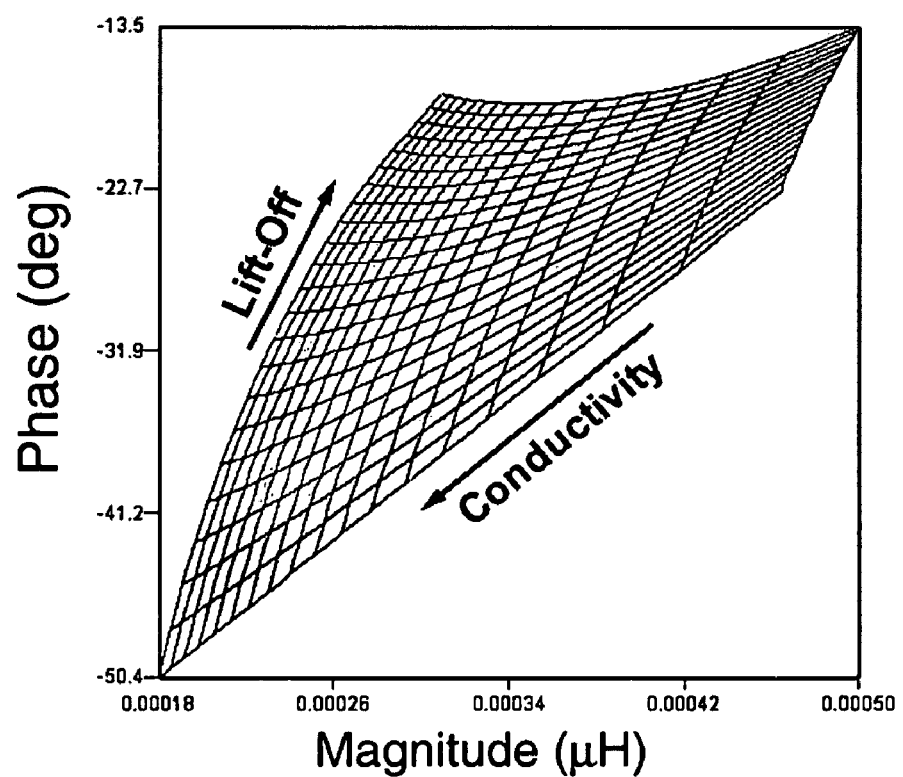
FIG. 4 shows a representative measurement grid relating the magnitude and phase of the sensor terminal impedance to the lift-off and electrical conductivity.

For ferromagnetic materials, such as most steels, a measurement grid can provide a conversion of raw data to magnetic permeability and lift-off. A representative measurement grid for ferromagnetic materials is illustrated in FIG. 3. A representative measurement grid for a low-conductivity non-magnetic alloy (e.g., titanium alloys, some superalloys, and austenitic stainless steels) is illustrated in FIG. 4. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. The variation in the coating can be corrected at each point in the image to improve the measurement of permeability in the substrate for the purpose of imaging stresses. The effective property can also be a layer thickness, which is particularly suitable for coated systems. The effective property could also be some other estimated damage state, such as the dimension of a flaw or some indication of thermal damage for the material condition.

Figure 5:
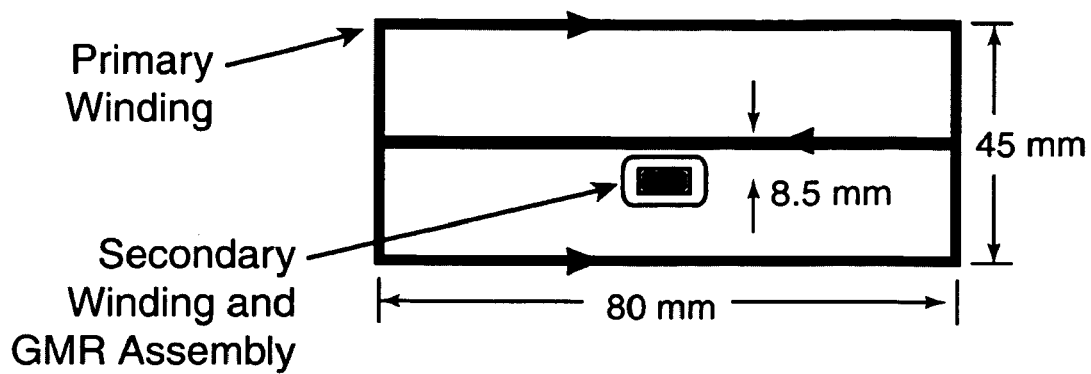
FIG. 5 shows a layout for a single turn Cartesian geometry GMR magnetomer.

In addition to inductive coils, other types of sensing elements, such as Hall effect sensors, magnetoresistive sensors, SQUIDS, Barkhausen noise sensors, and giant magnetoresistive (GMR) devices, can also be used for the measurements. The use of GMR sensors for characterization of materials is described in more detail in U.S. patent application Ser. No. 10/045,650, filed Nov. 8, 2001, the entire teachings of which are incorporated herein by reference. An example rectangular or Cartesian-geometry GMR-based magnetometer is illustrated in FIG. 5. Conventional eddy-current sensors are effective at examining near surface properties of materials but have a limited capability to examine deep material property variations. GMR sensors respond to magnetic fields directly, rather than through an induced response on sensing coils, which permits operation at low frequencies, even DC, and deeper penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations.

Figure 6:
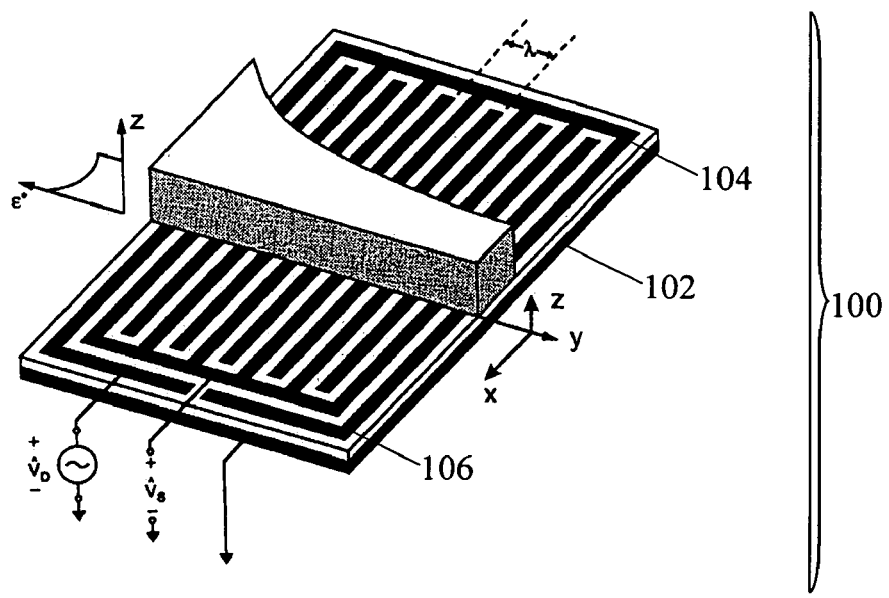
FIG. 6 shows a representative single wavelength interdigitated electrode dielectrometer with spatially periodic driven and sensing electrodes of wavelength $\lambda$ that can measure dielectric properties of the adjacent material for remotely monitoring the temperature of a plate.

For insulating or weakly conducting materials such as fiberglass composites, capacitive or dielectric sensors can be used. The sensors are the electromagnetic dual to the inductive sensors, with electric fields taking the place of magnetic fields for inspecting the materials and can be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing, except that the sensors operate in the electroquasistaic (EQS) regime. In one such electric field method multiple layers of material are added to a base material with each layer sensitive to different chemicals or biological materials. A representative single sided sensor geometry is shown in FIG. 6. The application of a sinusoidally time varying potential of angular frequency $\omega = 2\pi f$ results in the flow of a terminal current, whose magnitude and phase is dependent on the complex permittivity of the material. The capacitive sensor 100 has interdigitated electrodes as presented in U.S. Pat. Nos. 4,814,690, 6,380,747, and 6,486,673 and in U.S. patent application Ser. Nos. 10/040,797, filed Jan. 7, 2002, and 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage $v_D$ while the other, 106, is connected to a high-impedance buffer used to measure the magnitude and phase of the floating potential $v_S$ or to a virtually grounded amplifier to measure the magnitude and phase of the terminal current I. The periodicity of the electrode structure is denoted by the spatial wavelength $\lambda = 2\pi/k$, where k is the wavenumber.

Figure 7:
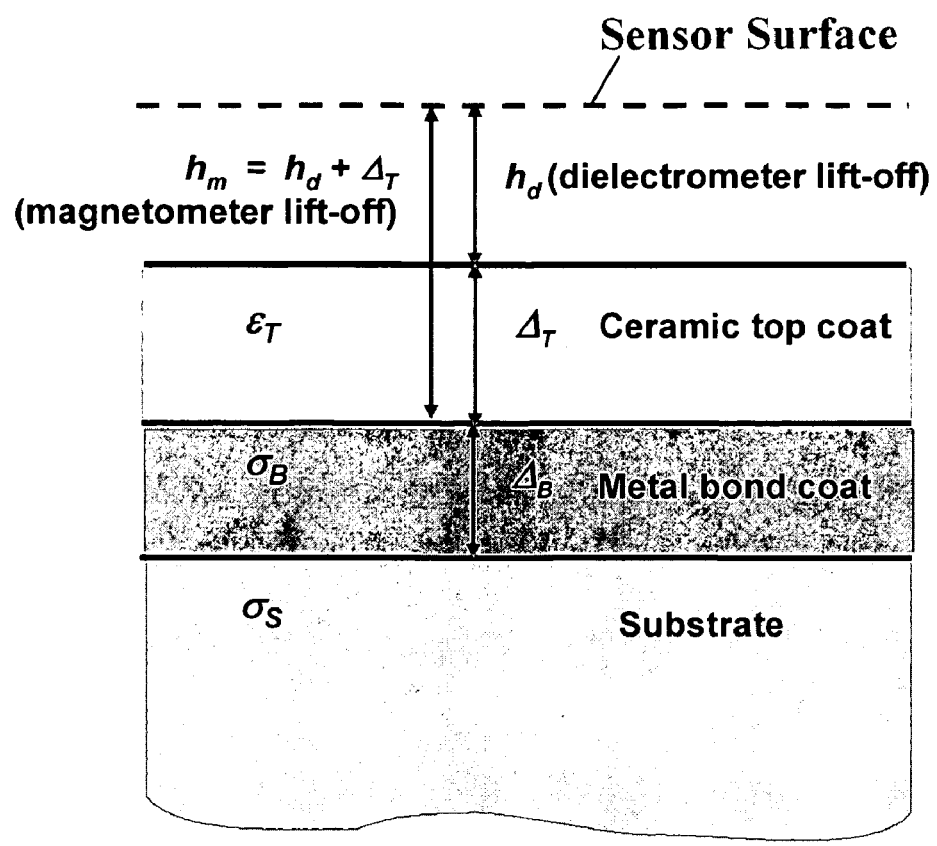
FIG. 7 shows a representative multi-layered coating system such as a ceramic top coat and a MCrAlY bond coat.

Each of these sensors can be used to provide information about the various layers in complex materials, such as a TBC. A representative TBC layer is illustrated in FIG. 7. The magnetometer (e.g., MWM) is sensitive to the magnetometer lift-off ($h_m$), which is the sum of the "physical" magnetometer lift-off and the ceramic thickness (to magnetic fields a dielectric material is indistinguishable from air), the thickness of the bond coat ($\Delta_b$), the permeability of the bond coat ($\mu_b$), and the conductivities of the bond coat and the substrate ($\sigma_b$ and $\sigma_s$, respectively). Multiple-frequency operation, possibly together with a segmented-field design, can be used to simultaneously estimate four or more unknowns. In turn the dielectric sensor (e.g., IDED) is sensitive to the lift-off ($h_d$), the ceramic top coat thickness ($\Delta_t$), and its dielectric permittivity ($\epsilon_t$), which in turn may be correlated with the microstructure, microstructural defects, and/or thermal conductivity of the coating. With two different dielectric wavelengths, two of these properties may be estimated independently. The hybrid operation makes it possible to eliminate one of the unknowns in the dielectric sensor by using the top coat thickness information from the magnetometer.

While measurement results from independent magnetometer and dielectrometer measurements can be combined to fully characterize the properties of a TBC system, it can be improved further by locating the magnetometer and dielectrometer within the same footprint. This will ensure that both sensing regimes see the same lift-off and, more importantly, the exact same location on the material under test. A hybrid sensor has other practical advantages as well, including not having to swap probes and being able to process data from both regimes simultaneously.

Another advantage is the reduction of unknowns that need to be determined from the dielectrometer sensor. In a typical application, there are three unknown properties of the ceramic top coat: thickness, dielectric permittivity (related to both the material's microstructure and its thermal conductivity), and lift-off (i.e., due to "air" gaps). Note that for dielectrometry the lift-off does not include the ceramic thickness, only contributions to the "air" gap, such as surface roughness or mismatched curvatures. It is in principle possible to use a three-wavelength IDED to measure these three unknown properties. A two-unknown estimation, however, is much less vulnerable to noise, due to the higher selectivity of the two-unknown method. A co-located MWM can provide an independent and highly accurate measurement of the sum of the thickness and lift-off, thereby reducing the number of unknowns to two, or allowing the third unknown, e.g., ceramic coating thickness, to be used as a redundant unknown for both the MQS (MWM) and EQS (IDED) sensors. A further advantage of using a hybrid sensor is that properties of both the metallic and nonmetallic layers of the coating system can be characterized simultaneously, again avoiding the addition of another unknown lift-off.

Figure 8:
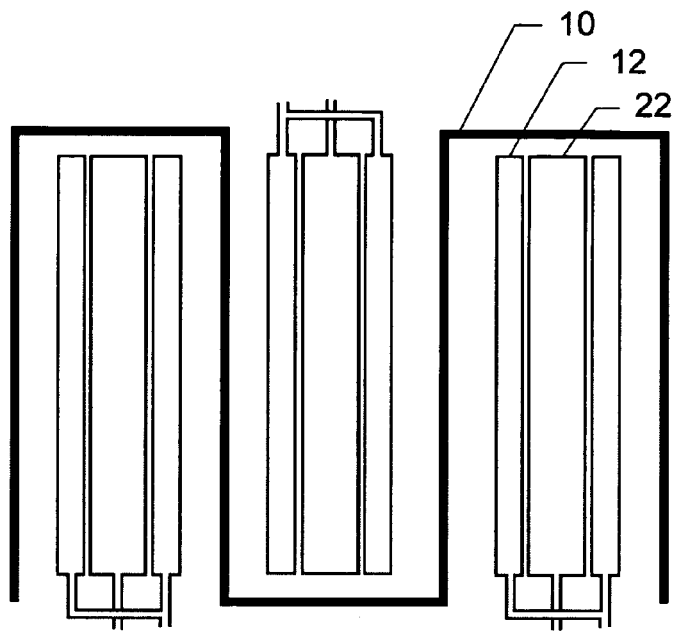
FIG. 8 shows a hybrid segmented-field MQS/EQS sensor with two different effective wavelengths in both modes.

In the simplest case, the basic MWM design shown in FIG. 1 can be used as an IDED by using the primary winding as the driven electrode and the secondary as the sensing electrode, as described for example in U.S. Pat. No. 5,453,689. However, an MWM optimized for magnetometer measurements would make a poor dielectrometer, because the secondary is too close to the primary and almost all of the electric field would be confined to the gap between them. A compromise is illustrated in FIG. 8, where the secondary windings are positioned far enough from the center to let them link enough magnetic flux when operated as an MWM, while allowing for a gap large enough to let the fringing electric fields penetrate into the material when used as an IDED. The secondary windings on either side of the primary are connected in series.

Figure 9:
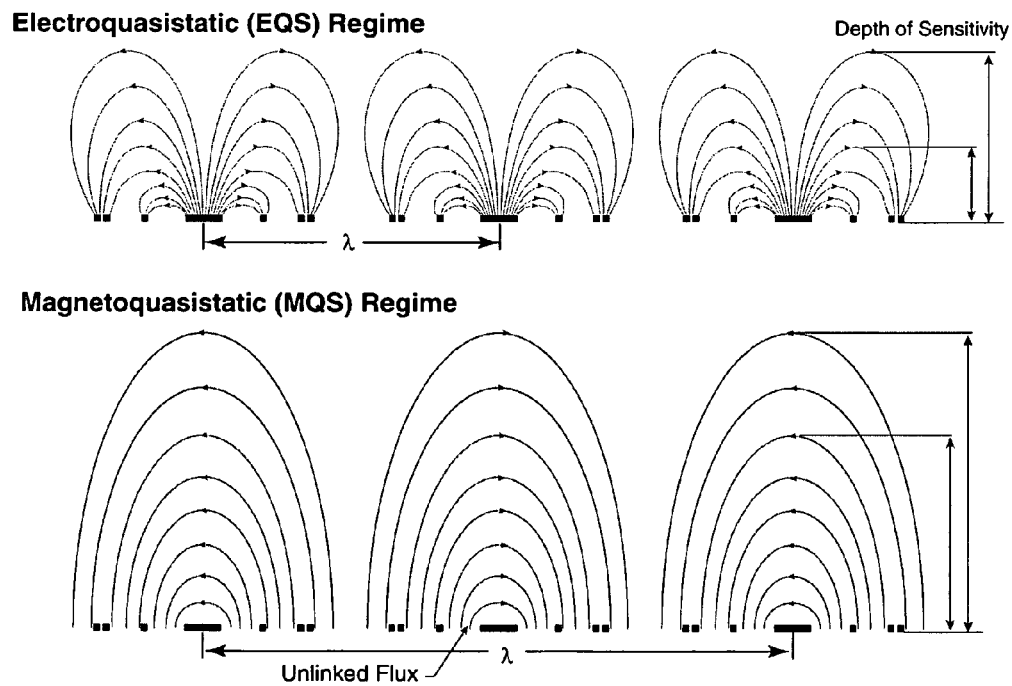
FIG. 9 shows electric and magnetic field lines of the hybrid sensor from FIG. 8.

Two secondary windings are present to provide co-located segmented-field operation in both the EQS and MQS regimes. The need for more than one secondary winding for segmented-field operation in the MWM regime is much lower than in the IDED regime because, unlike EQS operation, the depth of sensitivity of the magnetometer may be varied by operating the sensor at different frequencies, thus providing the additional constraints needed for multiple-unknown estimation. Nonetheless, the hybrid sensor layout in FIG. 8 has two segmented field outputs in both regimes. The electric field and magnetic field patterns in the two regimes are shown in FIG. 9. Note that the characteristic spatial wavelength of the hybrid sensor is twice as long in the MQS regime as in the EQS regime. For TBC characterization, this is advantageous since the dielectric measurement needs to be most sensitive to the ceramic top coat, while the magnetic measurement needs a greater depth of sensitivity in order to resolve features of the substrate and the bond coat, while penetrating through the top coat.

In a similar fashion these quasistatic sensing methods can also be applied to thermal variants and hybrid configurations. As an example, consider FIG. 10, where current through a drive winding 10 can be used to create a magnetic field for sensing with inductive elements and also heating of the test material 68. Typically, the heating effect is accomplished with a lower excitation frequency than the signal used to measure the inductive properties of the test material. The heating of the drive winding could be through resistive losses in the winding itself or through the induced eddy currents in the test material. Also for heating purposes the current through the drive winding can be enhanced, as is commonly performed with induction heating coils, by placing one or more capacitors in series or parallel with the drive winding. The parallel or series connection of the capacitor depends upon the electrical source used to drive the winding. In addition, one or more thermal sense elements 64 can be placed in the vicinity of the drive winding to sense the temperature of the test material. These thermal sense elements can be thermistors, thermocouples, or other temperature sensitive devices. For example, pyroelectric sensing elements, described for example in U.S. Pat. Nos. 4,332,157, 4,453,405, and 4,551,425, and can be used in the thermal regime to provide a voltage in response to a temperature gradient. The sense elements 66 can also be intermingled with the inductive sense elements. Furthermore, the temperature of the test material can also be varied with alternative sources 62 such as heat lamps or lasers typical of other thermal nondestructive inspection methods. However such heat lamps and laser are not easily surface mountable or embeddable.

Figure 10:
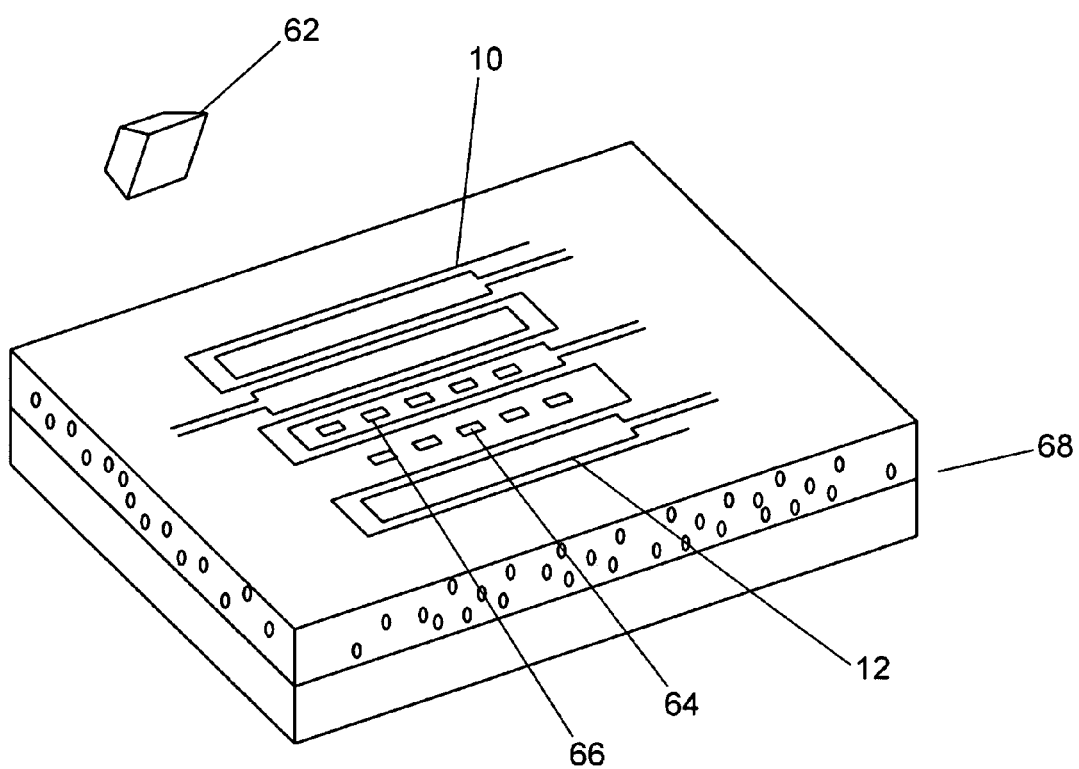
FIG. 10 shows an illustration of a hybrid sensor design having multiple source and sense modes.

The sensor of FIG. 10 is an example of a thermomagnetic (or thermal-magnetic) sensor that combines thermal and magnetic fields. The sensor can have one or two excitation source and one or two sensing modes as well. For example, to inspect or monitor the condition of a graphite/epoxy composite, a thermal source might be used to change the temperature of the composite during manufacturing (e.g. an oven) or in-service, then the transient in temperature of the material (fibers and matrix) might be observed using magnetic sensing methods with a magnetic source (as in an MWM or MWM-Array). This in itself would be a simple hybrid method, but in addition, a temperature sensing or imaging method, as used in thermal NDI methods, might also be used at the same time. Since the MWM will be sensitive to the properties of the fibers only and the thermal method will be sensitive to the fiber properties and the epoxy matrix properties, then the damage or condition of each material can be separated and even the bond integrity might be isolated. Note that the fibers and matrix temperature may vary at different rates, this would be modeled and precomputed databases could be used as for the MWM and IDED to improve the estimation of multiple unknown properties through measurements under numerous operating conditions, e.g. temperatures in this case. Allowable trajectories through hypercube space for the properties of the fibers and matrix can be used to constrain the unknown solution space, improving the reliability of the estimates. The graphite fiber composite is one example of a multiple component material system. The different components could also be different material layers, such as a TBC.

Thermoelectric sensors combine thermal and electric field sensing modes. An example material is a glass fiber or ceramic matrix composite (CMC) where the constituent materials have a relatively low electrical conductivity so that magnetic field sensors are not sensitive to the material condition. Since the dielectric properties, particularly the electrical conductivity, of most dielectrics varies with temperature, the dielectric constant and conductivity can be monitored with a capacitive sensor as the temperature is changed over time. This is similar to the monitoring of cure state of dielectric materials such as epoxies. The temperature can be changed by pulsing with a heat lamp or other temperature controllers, such as pyroelectric or Peltier devices. These devices may also be mounted proximate to or within the capacitive portion of the sensor. During the transient, the temperature of the fibers and the matrix change at different rates, which can provide information about the composites, such as the porosity, the presence of delimination, and the quality of the bond between the fibers and the host matrix.

This can also be extended that operate in more than two modes. For three modes, tribrid sensors can provide complementary information about the test material condition. For example, a thermoelectrosonic variant has thermal, capacitive, and acoustic modes. In this mode, the acoustic mode can be used to induce vibrations in the fibers of a composite. The acoustics response can be sensed directly as a sonic effect or through the coupled effect on the thermal or capacitive mode to detect disbonds or local defects. Another example is a thermoelectromagnetic variant having thermal, inductive (magnetic field) and capacitive (electric field) sensing capabilities. This type of sensor is well suited to the characterization of TBCs, which protect metallic substrates with an insulating ceramic coating over an intermediate metallic bond coating.

Furthermore, in each case an external or internal loading source might be used to vary the unknown, and possibly the known, properties of the material under test in a static, transient, quasistatic, and dynamic manner. An example of transient loading is applying a constant load and then removing the load to observe the resulting material response. An example of a quasistatic or steady-state load is to apply a load that varies slowly with time so that higher order dynamic terms can be ignored in models for the material response. In these cases, this loading enables property measurements to be made at multiple operating conditions, providing more equations to estimate these unknowns using the inversion methods.

These loads can take a variety of forms. Mechanical loading allows the stress or strain to be varied. Thermal loading varies the temperature of the materials. Magnetic loading could use a bias magnetic field to vary the operating point on a hysteresis loop for the magnetic properties. Electric loading can be performed, for example, by depositing electrical charge on the material. Sonic or acoustic methods can be applied to provide a cyclic load either locally or globally over broader regions. Kinematic loading can result from motion or impact and might be used to provide dynamic stress excitations. These loads might be applied as part of a manufacturing process or through typical or intentionally altered in-service loading. For example, measurements could be performed on a landing gear with and without fuel and/or with wheels up or during vibrations caused by taxiing or induced motion.

Figure 11:
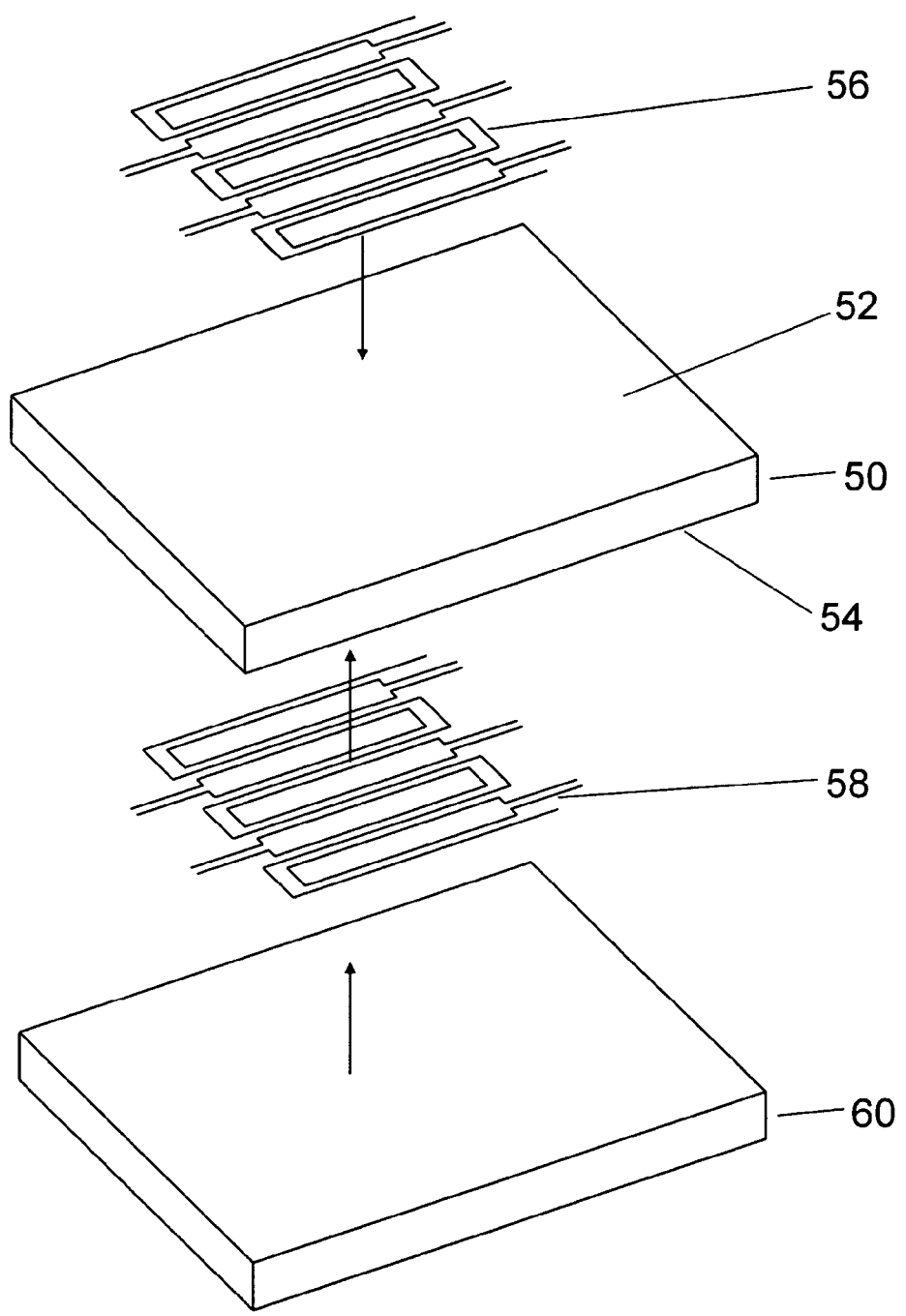
FIG. 11 shows an illustration of sensor segments positioned on accessible and hidden material surfaces.

In all of these cases the drive source or sources from each mode might be embedded between layers, within the matrix (e.g. as fibers), or at a hidden surface or on an opposing surface, or surface mounted on an exposed surface. This is illustrated FIG. 11, where sensor segments 56 are positioned on an accessible surface 52 of a test material layer 50. Additional sensor segments 58 can be placed on a hidden surface 52 where only access to the electrical leads to the segments are required. The sensor segments 58 may also be embedded with additional material such as the layer 60. In each case, the sensor segments may serve as drive conductors or sense elements. For example, in one embodiment continuous metallic or even graphite fibers might be used to carry current through the matrix, with an array of inductive sensing elements permanently mounted or scanning on the external surface. For the same system, higher currents might be used to provide inductive or resistive heating with thermal imaging at an embedded or exposed surface or simple point temperature measurement means, e.g. thermocouples, to monitor temperature at selected locations to provide sufficient observability.

Furthermore, the methods of embedding state sensitive material layers as described in U.S. patent application Ser. No. 10/937,105, filed on Sep. 8, 2004, the entire teachings of which are incorporated herein by reference, can also be applied. This includes burying magnetic materials between layers with either sensing elements and/or drive windings located in the same plane or in different planes at any planer position relative to the buried layer. For example, a magnetic layer might be located within the lap joint of an aircraft with the sensor drive and sensing elements located on the inside (exposed) surface of the aircraft to monitor stresses between skins of the aircraft, or the sensing elements might be mounted between the layers with the drive on the inside, exposed surface of the aircraft. This latter embodiment has the advantage that one failed sensing element will not bring down all other elements, and the drive windings are not at the faying surface so they are less likely to fail. In all cases, the stress gages can be used to detect and monitor stress redistributions associated with damage from fatigue, corrosion or other mechanisms.

In one embodiment, an MWM/IDED type format might be embedded at the interface between a metal and a composite, where the MWM sensor is used to measure the metal properties and any conducting or magnetic material properties of the composite, while the electric field sensor is used to measure the composite properties of the matrix and fibers. Furthermore, in one embodiment the sensors are used to monitor the curing and conditions of the adhesive bond and or the epoxy curing. In another embodiment the electric field sensor detects and measures moisture ingress. In another embodiment, external loads are used to alter the operating conditions to enhance measurement reliability and observability of multiple unknowns.

In each of these cases the sensors can be used independently with the data fused into a measurement grid or higher-order lattice. The data from each sensor can be combined in the same way that multiple frequencies are used for single mode sensors, such as the MWM, where there is a lattice for each sensor where all of the property estimates are performed at the same time. Alternatively, data from a sensor can be input on one axis while data from one or more other sensors are input on the other axes for the grid or lattice.

Figure 12:
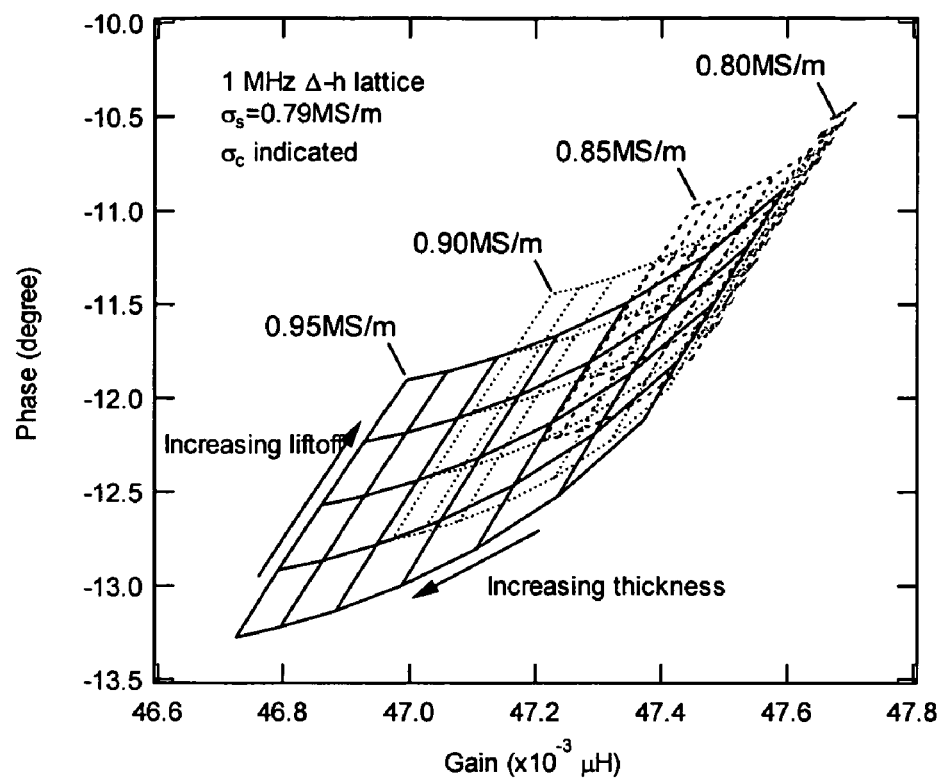
FIG. 12 shows a representative coating thickness/lift-off grid lattice for turbine blade materials.

As an example of a grid lattice, used for characterizing conducting coatings, measurement grids are created for a range of coating conductivities that span the range of interest for a given material, forming a three-dimensional database for the sensor response. A representative grid lattice for the characterization of turbine blade coatings is shown in FIG. 12. The lattice shows coating thickness-lift-off grids for four coating conductivities at a single frequency. In each measurement grid, the spacing between the grid points illustrates the sensitivity for independently estimating the coating thickness and the lift-off. The grid spacing and sensitivity is large when the coating and the substrate have significantly different conductivities; the grid collapses when the conductivities of the coating and the substrate are equal, which is expected for an uncoated specimen.

To characterize the coating, measurements are used with grid lattices at multiple excitation frequencies to determine a set of coating properties (such as conductivity, thickness, and lift-off) that are independent of frequency. Alternatively, iterative methods can be used to minimize the error between the predicted response from a model for the property variations with depth and the measured data at multiple frequencies and/or multiple lift-offs. Computationally, the grid lattice approach, which only uses table look-ups and simple interpolations, tends to be faster than the iterative approaches that require multiple calculations from a simulation model.

Another aspect of this invention uses the capability of model based sensor arrays to simultaneously obtain multiple property measurements for a given material during a single test. This allows statistical populations of property measurements to be correlated with material condition, such as fatigue, without having to create a large number of specimens. This can provide a tremendous cost savings, particularly when the specimen cost is very high and statistically valid method characterization, such as obtaining probability of detection curves and receiver operator curves, would otherwise not be possible.

Figure 13:
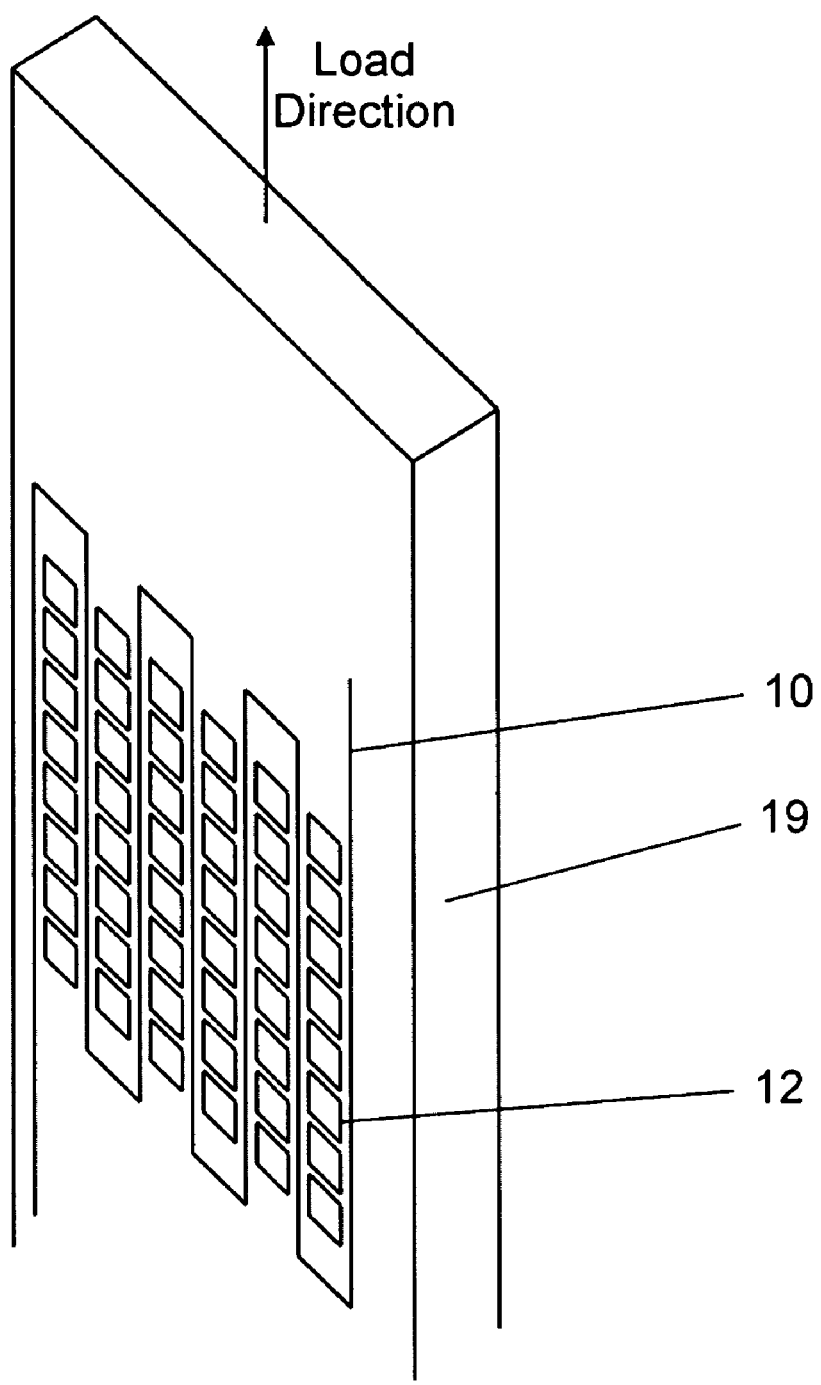
FIG. 13 shows an illustration of a sensor array placed over a test material being loaded.

In these test, for example with an MWM-Array, many test can be carried out simultaneously with each resulting signal representing a set of properties of a relatively small test volume. This is illustrated in FIG. 13, where a single drive winding 10 and multiple sense elements 12 are placed over a test material 19. The measured quantities are typically the lift-off, resistivity, conductivity and permeability. For example, resistivity can provide a unique measure of plastic deformation and crack development. Measuring resistivity with an array at many locations provides information of the electrical uniformity of a given sample, which could then be characterized by its mean value and its standard deviation. A similar set of data can be obtained fro the permeability of ferromagnetic materials.

Of particular usefulness is the statistical characterization of the fatigue behavior of a given material. Since crack growth is a fairly well defined and understood phenomenon, experimental scatter of fatigue data is primarily an initiation effect. In a specimen subject to uniform fatigue cycling, damage will progress to a certain level after different numbers of cycles at different locations. From a record of sensor outputs versus the number of cycles for which a given stage of damage is reached, a Weibull plot can be constructed. Usually this takes the form of $\ln(\ln(1/(1-P)))$ versus $\ln(N)$ where N is the number of cycles to achieve the specified damage level and P is the probability of failure. The probability of failure can be expressed as the number of sense elements having reached a particular level divided by the total number of sensors. Fatigue data usually fall on a straight line of slope m, with m called the Weibull modulus. In other words, $(1/(1-P))=\exp\{(N/No)^m\}$, where No is a constant. Thus, this allows information to be obtained about the scatter of fatigue lives for a test material from a single sensor array test. Another variation of this arrangement would be a longitudinal specimen containing, for example, 10 holes that are instrumented and being monitored with sensors. In this variant, the predicted failure probability also pertains to the stress distribution of the hole geometry that is used.

This type of tracking of the changes in the statistics of the population of response measurements can be performed on both fatigue test components as well as actual aircraft. The tracking can be performed with respect to the cumulative loading history, such as the actual number of fatigue cycles or a time based measured. This time based measure may relate to the number of load cycles or the number of flight hours. Furthermore, statistical analysis can also be applied to subpopulations of the responses that are separated from the main population. For example, the subpopulation might be components from a single aircraft, a single supplier, a single time period, or from a single geographic area. Tracking this subpopulation can influence the decisions to rework, repair, or replace component, as described for example in U.S. patent application Ser. No. 10/763,573, filed Jan. 22, 2004, the entire teachings of which are incorporated herein by reference.

Another aspect of this invention is directed toward the profiling and mapping of stress and other properties in magnetically permeable and other media. Typically, strain gage rosettes, i.e., two or more strain gages in different orientations, can be used to estimate strains in the plane of a surface. In the case where the principal stress directions are unknown, three gages are required in different directions to determine both the direction and magnitude of the principal strains for a biaxial stress state. If the principal directions are known, then only two strain gages are required.

Figure 14:
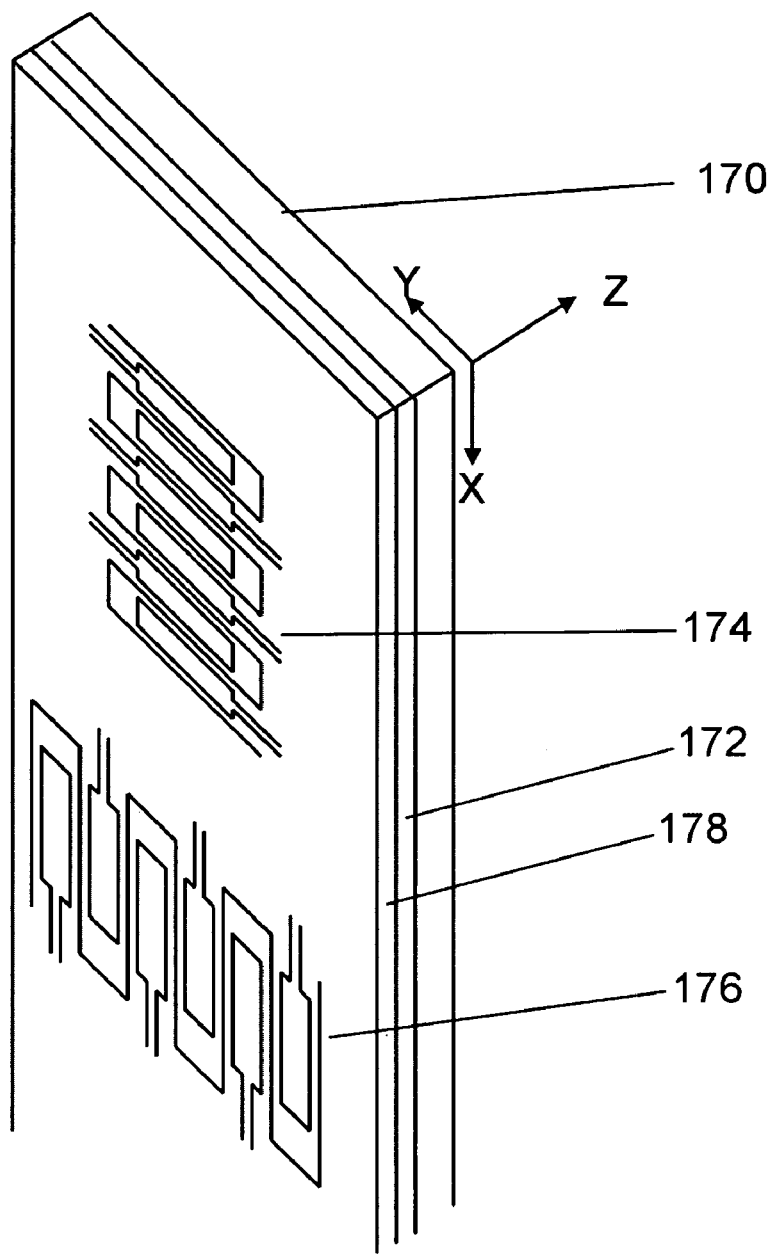
FIG. 14 shows a schematic drawing of two MWM-Arrays placed on a test material surface and oriented in different directions.

Profiling stress as a function of depth and or mapping as a function of surface position the properties of a conducting or insulating magnetic materials is achieved by measuring the permeability and/or conductivity in two or more directions and at multiple frequencies. The sensor for the measurements is designed to minimize the contribution from the property in other directions for any selected direction. The permeability and/or conductivity values are then correlated with the stress, as described in U.S. patent application Ser. No. 10/937,105. The two or more frequencies permit depth estimation for the higher or lower stress region near the surface of the MUT. This is best done using a model to represent the region of differing stress as a layer near the surface or as a predetermined distribution of properties as a function of depth. The property values that represent the properties of the layers or the spatial distribution with depth can then be determined using grid methods, as described earlier, along with sensor lift-off. FIG. 14 shows an example measurement configuration. The base material 170 can be a flat or curved component with physically distinct surface layers 172 and 178 or with the region of differing stress represented by one or more material layers near the surface. The MWM-Arrays 174 and 176 are oriented in perpendicular orientations to be sensitive to arbitrary orientations for the principal stress directions.

Figure 15:
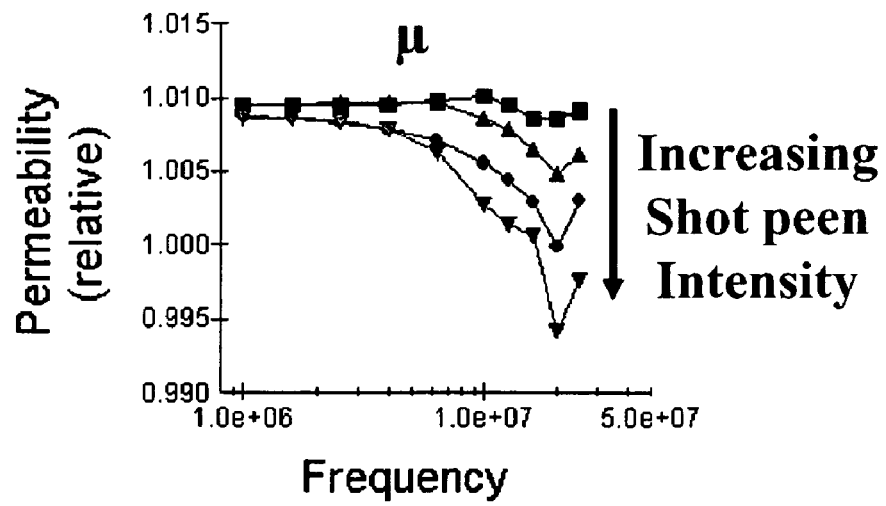
FIG. 15 shows an effective permeability plot as the frequency and shot peen intensity is varied assuming a constant conductivity.
Figure 16:
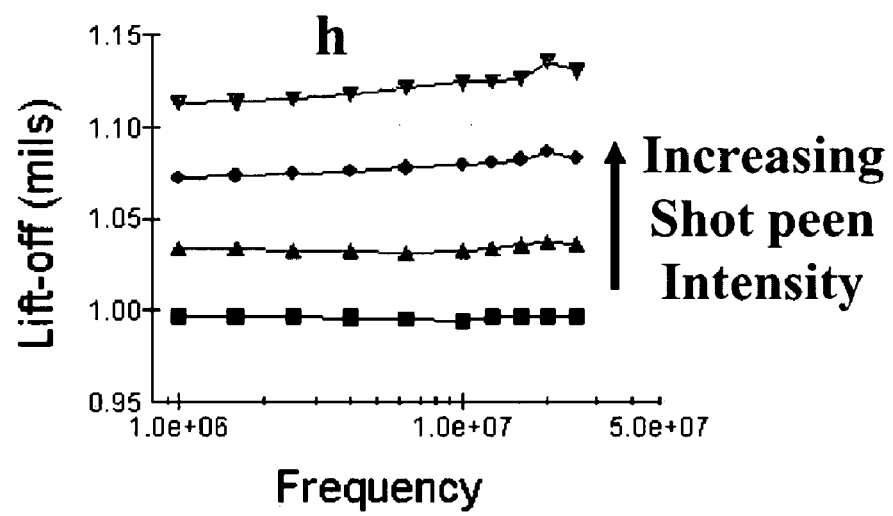
FIG. 16 shows an effective lift-off plot as the frequency and shot peen intensity is varied assuming a constant conductivity.

As an example, this stress profiling method can be used to qualify the shot peening process in relative low magnetic permeability materials. Many Nickel-based alloys and other materials begin with relatively low magnetic permeability before shot peening. For example, in IN718 or IN100 alloys the relative permeability is on the order of 1.01. At high frequency, for these alloys, shot peening decreases the permeability to ~1.00, as shown in FIG. 15. The effective lift-off, shown in FIG. 16, also varies with shot peening intensity. These effecs can be used to qualify shot peen intensity. At sufficiently high frequencies, the magnetic field is confined near the surface of the MUT and reflects mainly the stress of the surface region. At lower frequencies, the magnetic field can penetrate through this region and the average or effective property (permeability or conductivity) approaches the bulk value. The response is measured as a function of frequency and used to estimate one or more properties of the material with a model that represents the stress variation in the MUT as a surface layer or a predetermined distribution of properties as a function of depth. Grid methods used to estimate the properties of the layer, lift-off and the substrate, or the parameters of the distribution.

For cold work processing, such as shot peening, roller burnishing, low plasticity burnishing, and laser shock peening, the spatial property distribution as a function of depth can be split into several predetermined component layers. An example is a four layer systems, having a lift-off layer, a machining zone of thickness, a compressive residual stress zone, and a substrate. FIG. 14 shows an example substrate 170, residual stress layer 172, and machining zone 178. Representative thicknesses of the machining affected zone are 0.0005 to 0.002 in. and for the residual stress layer are 0.001 to 0.005 in, but the thicknesses will depend upon the material type and the cold work (e.g., shot peening) intensity. The properties of the different layers can be determined independently, possibly with assumed thicknesses, so that the cold work process intensity itself is then correlated with the properties, such as the magnetic permeability or conductivity, of the residual stress layer. The properties can be determined using the grid methods and precomputed databases of responses. To help to isolate the properties of the residual stress layer, the properties of the test material can be measured before and after the cold work process. These properties can be normalized by the before response, possibly by a simple ratio of difference, to highlight the change by the cold working. Similarly, to isolate the properties of the machining affected zone, the properties can be measured before and after the machining process. In all cases, spatial imaging with high resolution arrays scanned over the surface permit the measurement of local stress relaxation and can be used to determine when re-processing is necessary. Anisotropy in the properties can be measured with sensors having a directional bias, such as those having a linear, rectangular, or elliptical drive windings.

In some measurements inhomogeneous material properties in the unpeened material were found to be a significant source of 'noise' for this measurement. Consequently, a reference calibration was performed on a lightly peened area where it was assumed that the light peening would homogenize at least the surface layer and provide a more reliable reference. Further averaging was performed by continuously moving the sensor over the material surface. The measurement procedure then had the following steps: (1) Determine baseline properties of the substrate in a lightly peened region. (2) Reference calibrate on the lightly peened region. (3) Measure on more heavily peened regions, with an emphasis on the high frequency properties. Alternatively, the sample could be calibrated on robust reference pieces where the properties are well known.

As another example, this type of stress measurement can be used to determine bond strength of a coating by mapping the stresses at the interface. This is accomplished by mapping the magnetic permeability near the surface of one or both of the adjacent layers or a remote layer that sees a fraction of the stress. The permeability is then correlated to the stress on the coating. One of the layers, such as the coating, can be non-magnetic (relative permeability of 1.0). The measurements are typically performed in a scanning mode with the sensor and the MUT in relative motion so that an image of the bond quality is produced.

Another aspect of this direction is directed toward determining the stress in the direction normal to the free surface. As shown in FIG. 14, this is the z direction. No reliable nondestructive method (other than X-Ray diffraction under ideal circumstances) currently exists to measure the stress in the direction perpendicular to a free surface. Here, the tri-directional stresses in a component, including the stress in the principal directions and the stress in the direction normal to the free surface, is measured by using an MWM, MWM-Array or other directional magnetic property measurement sensor that is sensitive to variations in either the magnetic permeability or Barkhausen noise or other magnetic variation in two more directions including the normal direction.

The measurement of the normal component of the magnetic permeability is made possible by the inclusion of a permeability tensor in the formulation of transfer relations for magnetic materials. Although aspects of this modification have been described for example in U.S. Pat. No. 5,453,689, the extension of this analysis to obtaining the normal component of the permeability was not. To illustrate the implications of the tensor formulation, consider a layer of uniform material that is described by a permeability tensor with only diagonal elements $$\bar{\bar{\mu}} = \begin{bmatrix} \mu_x & & \\ & \mu_y & \\ & & \mu_z \end{bmatrix} \quad (1)$$

where $\mu_x$ and $\mu_y$ are in-plane magnetic permeabilities and $\mu_z$ is out-of-plane permeability and the coordinate system is relative to the orientation of the drive windings. A more complete derivation can be made with the additional off-diagonal elements included, but the diagonal elements are sufficient for this discussion. Solutions for the magnetic field in terms of the vector potential ($\bar{B} = \nabla \times \bar{A}$) in this layer have the form $$\hat{A}_x(z,y,t) = \hat{A}_o e^{-jky} e^{\gamma z} e^{j\omega t} \quad (2)$$

$$\gamma = \pm \sqrt{j\omega\sigma\mu_z + \frac{\mu_z}{\mu_y}k^2} \quad (3)$$

when the current in the drive winding (for example 10 in FIG. 1) is oriented in the x direction. Note that ω is the angular frequency, σ is the electrical conductivity, and μ is the magnetic permeability. Due to the direction of the induced current and fields, the sensor interaction with the material is insensitive to the $\mu_x$ component of the permeability, neglecting end effects. In other words, the in-plane component of permeability that is parallel to the drive orientation. However, the sensor is sensitive to both permeability tensor elements $\mu_z$ and $\mu_y$. The component $\mu_y$ is parallel to the surface and is also perpendicular to the drive winding direction. These components correspond to the are in-plane magnetic permeabilities and $\mu_z$ is out-of-plane permeability and the coordinate system is relative to the orientation of the drive windings. Independent estimates for $\mu_z$ and $\mu_y$ are then possible by performing multiple frequency measurements. At sufficiently high frequencies, the $\mu_z/\mu_y k^2$ term in Eq. 3 becomes negligible compared to the $j\omega\mu_z$ term so that $\mu_z$ can be estimated. In contrast, at sufficiently low frequencies the value of $\mu_y$ can be estimated. Note that rotation of the sensor changes the relative orientation of the reference frame for the sensor compared to the material properties. Consequently, rotation of the sensor by 90 degrees results in measurements which now include the same normal component $\mu_z$, but with $\mu_y$ replaced by $\mu_x$, where the coordinate directions for the permeability tensor elements are relative to the material reference frame. Since the permeability with respect to the sensor coordinates can be expressed as $$\mu_{sy} = \mu_y \cos(\theta-\theta_o) + \mu_x \sin(\theta-\theta_o)$$

$$\mu_{sx} = \mu_x \cos(\theta-\theta_o) + \mu_y \sin(\theta-\theta_o) \quad (4)$$

where $\mu_x$ and $\mu_y$ are the permeability tensor elements with respect to the material coordinates, $\mu_{sy}$ and $\mu_{sx}$ are the permeability tensor elements in the sensor reference frame, θ is the rotation of the sensor reference frame about the common z axis, and $\theta_o$ is a potential offset between the principle axis of the material and the unrotated sensor coordinate system. Three measurements of the permeability at sufficiently different and known angles θ then allow the estimation of $\mu_x$, $\mu_y$ and $\theta_o$. Grid methods or other methods can then be used to independently measure the magnetic permeability in the normal and surface direction (for example, the surface direction perpendicular to the longer MWM drive winding segments). Measurements taken with the same MWM in two directions can then determine the stresses in the plane and provide two independent measures of the normal stress. Finally, sensors can be layered with multiplexed drives or two sensors might be mounted on top of each other with drives simultaneously driving to provide an effective rotation of the drive field through 360 degrees, by varying the drive magnitude in each sensor continuously or incrementally or selectively.

The distributed magnetic field sensor and sensor array designs of FIGS. 1 and 2 can also be modified into a tape-like format for monitoring properties and damage to a material. An example of typical damage is localized corrosion along a relatively long structural support article. In such cases, it is convenient to roll the tape along the article and attach it with an adhesive. In an embodiment the sensing elements and drive are located on the same side of the test material with the drives running parallel to the longer dimension of the component being tested. The sensing elements can then be made relatively large between the drives without having a dead zone along the axis of the component. Bond pads can be placed at intermediate positions along the length of the tape so that cross-connections at the end of the tape, after being cut to match the length of the component being inspected, can be made relatively easily. In addition, for corrosion monitoring applications, a magnetizable thin layer coating can be applied over wide areas. Remotely scan or mount permanent sensors to monitor stress redistribution in layer for the purpose of detecting remote buried cracks, corrosion and anything else that may affect the redistribution of loads on that layer. In-situ determine of stress-strain curves can be obtained by apply strain gages and magnetic stress gages at the same location on an article. This could generate localized stress strain curves during loading and unloading or during life of an aircraft both with continuous monitoring and scheduled periodic inspections.

Signature Tolerance is a damage tolerance methodology applied to radar signature of RAM or LO coatings. Such RAM or LO coatings will degrade over time by measuring properties with MWM or other methods at scheduled inspection intervals. The life of coating areas can be extended and acceptable signature degradation limits can be set. Furthermore, such magnetizable LO coatings also will vary in properties as a result of substrate crack and corrosion damage. The stress change in LO coating from corrosion or cracks will change LO coating magnetic properties. Patterns of property variations over large areas can even be used to detect other remote damage to structural members. In addition, coatings can be enhanced to improve sensitivity to such damage.

During the insertion of a bushing, the bushing is first inserted then scanned with an MWM-Array while in place. The bushing is then cold-expanded in place. The MWM-Array is then scanned again to detect magnetizable permeability due to the cold working. In one embodiment, the bushing has a relatively thin magnetic layer on the outer surface. In the same embodiment, the bushing non magnetizable permeability (i.e., permeability=1) substrate on the inside. In this case, the MWM measures permeability of the outer layer to isolate the stress and/or stress change at the interface between the bushing and aircraft component or other structural member. The MWM can be scanned or permanently mounted. A bolt can then be inserted for fastening purposes. From time to time, the bolt can be removed and MWM can be used to scan, to map and/or track changes in stress distribution at the interface. This can be used with threaded or unthreaded "bushings" or sleeves.

While the inventions have been particularly shown and described with reference to preferred embodiments thereof, it will be understood to those skilled in the art that various changes in form and details may be made therein without departing from the spirit and scope of the invention as defined by the appended claims.

What is claimed is:

1. A method for characterizing a material property comprising:
    placing a sensor proximate to a test material having at least two component materials, said sensor providing at least one source field for nondestructively interrogating the test material;
    nondestructively loading the rest material by applying a second source field, the component materials having different material property changes with loading;
    measuring a response with the sensor, the sensor responding preferentially to material property changes in one of the component materials with loading by the second source field, wherein measuring the response further comprises measuring the at least one component property change with variation in the loading by the second source field; and
    converting the response into a characteristic of the test material.

2. The method as claimed in claim 1 wherein one source field is magnetic.

3. The method as claimed in claim 1 wherein one source field is electric.

4. The method as claimed in claim 1 wherein one source field is temperature.

5. The method as claimed in claim 1 wherein the loading source field is mechanical.

6. The method as claimed in claim 1 wherein the loading source field is acoustic.

7. The method as claimed in claim 1 wherein the loading source field is thermal.

8. The method as claimed in claim 1 wherein the loading source field is a laser.

9. The method as claimed in claim 1 further comprising applying a bias field with one of the source fields.

10. The method as claimed in claim 1 wherein the second source field operates in a transient manner.

11. The method as claimed in claim 1 wherein the second source field operates in a steady-state manner.

12. The method as claimed in claim 1 wherein the second source field operates in a dynamic manner 13. The method as claimed in claim 1 wherein the test material property is electrical conductivity.

14. The method as claimed in claim 1 wherein the test material property is thermal conductivity.

15. The method as claimed in claim 1 wherein the test material property is dielectric permittivity.

16. The method as claimed in claim 1 wherein the test material property is magnetic permeability.

17. The method as claimed in claim 1 wherein the second source field is also applied by the sensor.

18. The method as claimed in claim 1 wherein converting each response further comprises:
    converting each response into the material property of an individual component.

19. The method as claimed in claim 1 wherein the sensor is a quasistatic sensor.

20. A method for characterizing a material property comprising:
    placing a sensor proximate to a rest material having at least two component materials, said sensor providing at least one source field for nondestructively interrogating the test material;
    nondestructively loading the rest material by applying a second source field, the component materials having different material property changes with loading, where one source field is magnetic;
    measuring a response with the sensor, the sensor responding preferentially to material property changes in one of the component materials with a loading by the second source field; and
    converting the response into a characteristic of the test material.

21. A method for characterizing a material property comprising:
    placing a sensor proximate to a test material having at least two component materials, said sensor providing at least one source field for nondestructively interrogating the test material;
    nondestructively loading the test material by applying a second source field, the component materials having different material property changes with loading;
    measuring a response with the sensor, the sensor responding preferentially to material property changes in one of the component materials with loading by the second source field; and
    converting the response into the material property of an individual component of the test material.

* * * * *

UNITED STATES PATENT AND TRADEMARK OFFICE
CERTIFICATE OF CORRECTION

PATENT NO. : 7,451,657 B2  Page 1 of 1
APPLICATION NO. : 11/036780
DATED : November 18, 2008
INVENTOR(S) : Neil J. Goldfine et al.

It is certified that error appears in the above-identified patent and that said Letters Patent is hereby corrected as shown below:

Claim 1, column 17, line 35, delete "rest" and insert --test--;

Claim 20, column 18, line 29, delete "rest" and insert --test--;

Claim 20, column 18, line 33, delete "rest" and insert --test--.

Signed and Sealed this

Tenth Day of February, 2009

JOHN DOLL
*Acting Director of the United States Patent and Trademark Office*